US012569147B2

(12) United States Patent
Sun et al.

(10) Patent No.: US 12,569,147 B2
(45) Date of Patent: Mar. 10, 2026

(54) FLUID RESPONSIVENESS DETECTION DEVICE AND METHOD

(71) Applicant: SHENZHEN MINDRAY BIO-MEDICAL ELECTRONICS CO., LTD., Shenzhen (CN)

(72) Inventors: Bailei Sun, Shenzhen (CN); Fei Han, Shenzhen (CN); Fei Zhang, Shenzhen (CN); Chunliu Xie, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 1131 days.

(21) Appl. No.: 17/489,966

(22) Filed: Sep. 30, 2021

(65) Prior Publication Data

US 2022/0015646 A1     Jan. 20, 2022

Related U.S. Application Data

(63) Continuation of application No. PCT/CN2019/080882, filed on Apr. 1, 2019.

(51) Int. Cl.
*A61B 5/02* (2006.01)
*A61B 5/00* (2006.01)
(Continued)

(52) U.S. Cl.
CPC ........ *A61B 5/02028* (2013.01); *A61B 5/0205* (2013.01); *A61B 5/02108* (2013.01);
(Continued)

(58) Field of Classification Search
CPC .............. A61B 5/02028; A61B 5/0205; A61B 5/02108; A61B 5/029; A61B 5/0295;
(Continued)

(56) References Cited

U.S. PATENT DOCUMENTS 8,246,546 B2     8/2012   Huiku et al.
2007/0179386 A1     8/2007   Michard et al.
(Continued)

FOREIGN PATENT DOCUMENTS

CN     106793959 A     5/2017
CN     107205674 A     9/2017
CN     108937881 A     12/2018

OTHER PUBLICATIONS

International Search Report issued in corresponding International Application No. PCT/CN2019/080882, mailed Dec. 13, 2019, 6 pages.
(Continued)

*Primary Examiner* — Tse W Chen
*Assistant Examiner* — Evelyn Grace Park
(74) *Attorney, Agent, or Firm* — Morgan, Lewis & Bockius LLP

(57) ABSTRACT

A liquid reactivity detection device and method. The liquid reactivity detection device includes: a breathing signal acquisition module, a hemodynamic signal acquisition module and a liquid reactivity detection module. The breathing signal acquisition module and the hemodynamic signal acquisition module work in cases where the subject is in any one of the following breathing modes: a spontaneous breathing mode, a spontaneous breathing combined with mechanical ventilation mode, and a mechanical ventilation mode. The hemodynamic signal acquisition module is configured to acquire at least one hemodynamic signal of the subject. The breathing signal acquisition module is configured to acquire at least one breathing signal of the subject. The liquid reactivity detection module is configured to determine the liquid reactivity of the subject according to the breathing signal and the hemodynamic signal.

15 Claims, 2 Drawing Sheets

(51) Int. Cl.

| | |
|---|---|
| *A61B 5/0205* | (2006.01) |
| *A61B 5/021* | (2006.01) |
| *A61B 5/029* | (2006.01) |
| *A61B 5/0295* | (2006.01) |
| *A61B 5/083* | (2006.01) |
| *A61B 5/087* | (2006.01) |
| *A61B 5/091* | (2006.01) |

(52) U.S. Cl.
CPC ............ *A61B 5/029* (2013.01); *A61B 5/0295* (2013.01); *A61B 5/0836* (2013.01); *A61B 5/087* (2013.01); *A61B 5/091* (2013.01); *A61B 5/4836* (2013.01); *A61B 5/7275* (2013.01); *A61B 2560/0266* (2013.01)

(58) Field of Classification Search
CPC ....... A61B 5/0836; A61B 5/087; A61B 5/091; A61B 5/4836; A61B 5/7275; A61B 2560/0266; A61B 5/08; A61B 5/0816
See application file for complete search history.

(56) References Cited

U.S. PATENT DOCUMENTS

| | | | |
|---|---|---|---|
| 2010/0191128 A1 | 7/2010 | Shelley et al. | |
| 2014/0073890 A1 | 3/2014 | Su et al. | |
| 2015/0327790 A1* | 11/2015 | Ushiroda | A61B 5/35 |
| | | | 600/518 |
| 2017/0273573 A1* | 9/2017 | Tusman | A61B 5/0836 |
| 2017/0360366 A1* | 12/2017 | Potes | A61B 5/0836 |
| 2018/0184945 A1* | 7/2018 | Borel | A61M 16/0051 |

OTHER PUBLICATIONS

First Office Action issued in related Chinese Application No. 201980093763.6, mailed Mar. 21, 2024, 6 pages.

* cited by examiner

120

FLUID RESPONSIVENESS DETECTION DEVICE AND METHOD

CROSS REFERENCE TO RELATED APPLICATION

This application is a bypass continuation of Patent Cooperation Treaty Application No. PCT/CN2019/080882, entitled "Liquid Reactivity Detection Device and Method," filed on Apr. 1, 2019, the content of which is hereby incorporated by reference in its entirety.

TECHNICAL FIELD

Embodiments of the disclosure relate to the medical electronic technical field and to, for example, a fluid responsiveness detection device and method.

BACKGROUND

In a clinical operation or circulatory support for critically ill patients, determination on a volume status is very important. When acute circulatory failure or insufficient tissue perfusion appears in clinic, volume expansion therapy is a common method for maintaining or improving organ perfusion, and good fluid responsiveness is a basic premise for volume expansion therapy. According to the Frank-Starling mechanism, only when both left and right ventricles are in an ascending branch of the cardiac function curve, the cardiac output can be significantly increased by means of increasing the cardiac preload through volume expansion therapy, i.e., achieving good fluid responsiveness. However, when one of the ventricles is in a platform branch of the cardiac function curve, it is difficult to further increase the cardiac output by means of increasing the cardiac preload, which exhibits poor fluid responsiveness, and blind volume expansion therapy may increase the risk of pulmonary edema.

At present, clinically, fluid responsiveness is predicted by means of monitoring a systolic blood pressure variability (SPV), a pulse pressure variation (PPV), a stroke volume variation (SVV), an inferior or superior vena cava diameter respiratory variation rate (transesophageal echocardiography/transthoracic echocardiography, TEE/TTE), an aortic peak blood flow rate variation rate $\Delta$peak (transesophageal echocardiography), a pre-ejection period variation (PEPV) and other dynamic preload parameters during breathing. At the same time, the current clinical application of dynamic preload is applied under limited condition of complete mechanical ventilation with a constant tidal volume (8-12 ml/kg) and without arrhythmia. The fluid responsiveness prediction method mentioned above has severe constraints and a narrow application range.

SUMMARY

The following is a summary of the subject matter detailed herein. This summary is not intended to limit the scope of protection of the claims.

Embodiments of the disclosure provide a fluid responsiveness detection device and method to detect fluid responsiveness in any breathing mode.

According to a first aspect, an embodiment of the disclosure provides a fluid responsiveness detection device, including: a breathing signal acquisition module, a hemodynamic signal acquisition module and a fluid responsiveness detection module, where the breathing signal acquisition module and the hemodynamic signal acquisition module operate under a breathing mode of a subject selecting from the group consisting of: a spontaneous breathing mode, a spontaneous breathing and machine-controlled breathing mode, and a machine-controlled breathing mode; the hemodynamic signal acquisition module is configured to acquire at least one hemodynamic signal of the subject; the breathing signal acquisition module is configured to obtain at least one breathing signal of the subject; and the fluid responsiveness detection module is configured to determine the fluid responsiveness of the subject based on the breathing signal and the hemodynamic signal.

In some embodiments, the breathing signal includes a respiratory cycle.

In some embodiments, the breathing signal further includes a respiratory amplitude.

In some embodiments, the breathing signal acquisition module is further configured to acquire a breathing state parameter of the subject, and extract the breathing signal of the subject based on the acquired breathing state parameter, where the breathing state parameter includes at least one of an airway pressure, an airway flow, a carbon dioxide flow, a tidal volume, a thoracic impedance signal, a magnetic signal, or a respiratory acoustic signal.

In some embodiments, the breathing signal acquisition module is further configured to determine a breathing envelope of the hemodynamic signal based on the acquired hemodynamic signal, and extract the breathing signal of the subject based on the breathing envelope.

In some embodiments, the hemodynamic signal includes at least one of a central venous pressure (CVP), a stroke volume (SV), a pulse oximetry plethysmograph (POP), a perfusion index (PI), a systolic arterial pressure (SAP), a pulse pressure (PP), a pre-ejection period (PEP), an inferior or superior vena cava diameter, and an aortic blood flow rate.

In some embodiments, the fluid responsiveness detection module is further configured to determine a respiratory variation of the subject based on the respiratory cycle, determine a hemodynamic variation of the subject based on the respiratory cycle, and determine the fluid responsiveness of the target subject based on the respiratory variation and the hemodynamic variation.

In some embodiments, the respiratory variation includes a respiratory variation trend, a respiratory variation rate, and a respiratory variation value, and the hemodynamic variation includes a hemodynamic variation trend, a hemodynamic variation rate, and a hemodynamic variation value;

the fluid responsiveness detection module is further configured to perform one of the following operations: determining the fluid responsiveness of the subject based on the respiratory variation trend and the hemodynamic variation trend; determining the fluid responsiveness of the subject based on the respiratory variation rate and the hemodynamic variation rate; and determining the fluid responsiveness of the subject according to the respiratory variation value and the hemodynamic variation value.

In some embodiments, the fluid responsiveness detection module is further configured to determine that the subject has good fluid responsiveness when it is determined that the hemodynamic variation and the respiratory variation meet variation correlation conditions of the hemodynamic signal and the breathing signal; and determining that the subject has poor fluid responsiveness when it is determined that the hemodynamic variation and the respiratory variation do not meet variation correlation conditions of the hemodynamic signal and the breathing signal.

In some embodiments, the fluid responsiveness detection module is further configured to determine a respiratory amplitude variation of the subject based on the respiratory cycle, determine a hemodynamic variation of the subject based on the respiratory cycle, and determine the fluid responsiveness of the target subject based on the respiratory amplitude variation and the hemodynamic variation.

According to a second aspect, an embodiment of the disclosure further provides a fluid responsiveness detection method, including: in any one of a spontaneous breathing mode, a spontaneous breathing and machine-controlled breathing mode, and a machine-controlled breathing mode, acquiring at least one hemodynamic signal of a subject; obtaining at least one breathing signal of the subject; and determining the fluid responsiveness of the subject based on the hemodynamic signal and the breathing signal.

In some embodiments, the breathing signal includes a respiratory cycle; accordingly, determining the fluid responsiveness of the subject based on the hemodynamic signal and the breathing signal includes: determining a respiratory variation of the subject based on the respiratory cycle; determining a hemodynamic variation of the subject based on the respiratory cycle; and determining the fluid responsiveness of the target subject based on the respiratory variation and the hemodynamic variation.

In some embodiments, the breathing signal further includes a respiratory amplitude, and accordingly, determining the fluid responsiveness of the subject based on the hemodynamic signal and the breathing signal includes: determining a respiratory amplitude variation of the subject based on the respiratory cycle; determining a hemodynamic variation of the subject based on the respiratory cycle; and determining the fluid responsiveness of the subject based on the respiratory amplitude variation and the hemodynamic variation.

In some embodiments, determining the fluid responsiveness of the subject based on a respiratory variation of the hemodynamic signal includes: determining that the subject has good fluid responsiveness when it is determined that the hemodynamic variation and the respiratory variation meet variation correlation conditions of the hemodynamic signal and the breathing signal; and determining that the subject has poor fluid responsiveness when it is determined that the hemodynamic variation and the respiratory variation do not meet variation correlation conditions of the hemodynamic signal and the breathing signal.

In some embodiments, the respiratory variation includes a respiratory variation trend, a respiratory variation rate, and a respiratory variation value, and the hemodynamic variation includes a hemodynamic variation trend, a hemodynamic variation rate, and a hemodynamic variation value.

After accompanying drawings and detailed description are read and understood, other aspects can be understood.

DETAILED DESCRIPTIONS

The disclosure will be further described in detail below with reference to accompanying drawings and embodiments. It can be understood that specific embodiments described herein are intended only to explain the disclosure, but not to limit the disclosure. In addition, it should be noted that, for ease of description, the accompanying drawings only show a part of the structure related to the disclosure instead of all of the structure.

Figure 1:
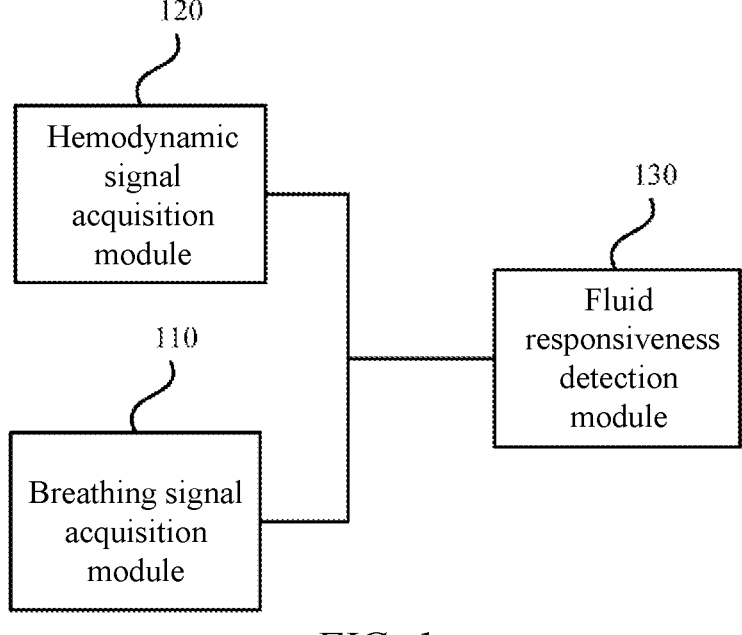
FIG. 1 is a schematic structural diagram of a fluid responsiveness detection device provided in the disclosure.

FIG. 1 is a schematic structural diagram of a fluid responsiveness detection device provided in the disclosure. As shown in FIG. 1, the device includes: a breathing signal acquisition module 110, a hemodynamic signal acquisition module 120 and a fluid responsiveness detection module 130, where the hemodynamic signal acquisition module 120 is configured to acquire at least one hemodynamic signal of the subject; the breathing signal acquisition module 110 is configured to acquire at least one breathing signal of the subject; and the fluid responsiveness detection module 130 is configured to determine the fluid responsiveness of the subject based on the breathing signal and the hemodynamic signal.

The subject may include all creatures with pulse signals, such as humans and animals.

In this embodiment, the breathing signal acquisition module and the hemodynamic signal acquisition module operate when a subject is in any one of the following breathing modes: a spontaneous breathing mode, a spontaneous breathing and machine-controlled breathing mode, and a machine-controlled breathing mode. The spontaneous breathing mode is a mode where a subject breathes without the assistance of a mechanical breathing device. The spontaneous breathing and machine-controlled breathing mode a mode where a subject breathes with the assistance of a mechanical breathing device, the gas that the subject breathes including oxygen provided by the mechanical breathing device and air that the subject breathes spontaneously. The machine-controlled breathing mode is a mode where the subject cannot breathe spontaneously, and the mechanical breathing device provides oxygen for the subject to breathe. In the machine-controlled breathing mode, the tidal volume is not limited to a fixed range, and can be adjusted as desired. In any of the above breathing modes, each breath of the subject may be different, and a normal breathing state of the subject may be accurately reflected. At the same time, hemodynamic information under varying breathing states can be obtained by acquiring hemodynamic signals of the subject in any of the above modes. The breathing signal acquisition module 110 and the hemodynamic signal acquisition module 120 operate synchronously and acquire a breathing signal and a hemodynamic signal of the subject simultaneously. In some embodiments, a breathing mode during fluid responsiveness detection can be determined based on the breathing mode of a subject during volume expansion therapy on the subject. In some embodiments, it is also possible to switch a breathing mode of the subject in the process of fluid responsiveness detection, obtain breathing signals and hemodynamic signals of the subject in different breathing modes, further detect the fluid responsiveness of the subject in different breathing modes, and comprehensively detect the fluid responsiveness, to improve accuracy of fluid responsiveness detection. The technical solution of this embodiment overcomes a limitation on a breathing mode during conventional fluid responsiveness detection, which determines the fluid responsiveness under spontaneous breathing or adjustable machine-controlled breathing of the subject, and improves applicability and accuracy of the fluid responsiveness detection.

Exemplarily, the hemodynamic signal acquisition module 120 includes a device or a sensor configured to acquire a hemodynamic signal. In some embodiments, the hemodynamic signal includes at least one of a CVP, an SV, a POP, a PI, an SAP, a PP, a PEP, an inferior or superior vena cava diameter, and an aortic blood flow rate. Accordingly, the hemodynamic signal acquisition module 120 may include devices or sensors respectively configured to acquire at least one of the CVP, the SV, the POP, the PI, the SAP, the PP, the PEP, the inferior or superior vena cava diameter, and the aortic blood flow rate. For example, the hemodynamic signal acquisition module 120 may include a blood pressure measuring instrument configured to measure an arterial pressure. It should be noted that, the devices or sensors respectively configured to acquire at least one of the CVP, the SV, the POP, the PI, the SAP, the PP, the PEP, the inferior or superior vena cava diameter, and the aortic blood flow rate may be independent, or two or more signal acquisition functions may be integrated in one device.

Figure 2:
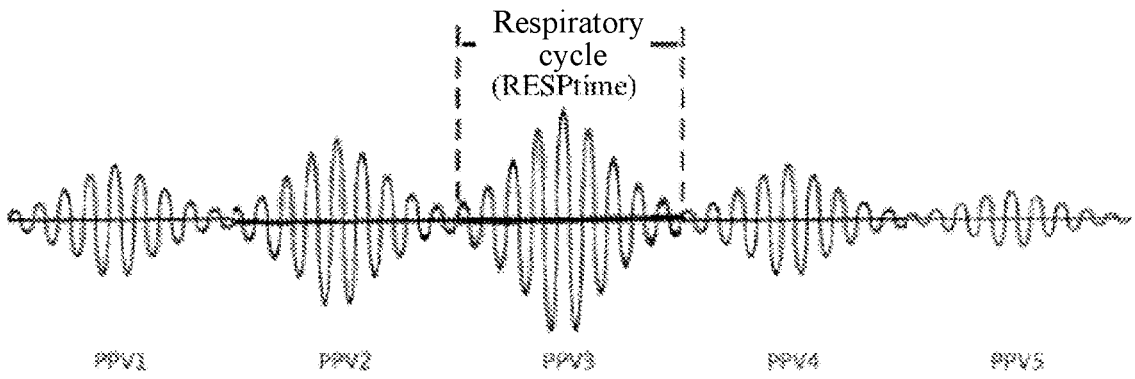
FIG. 2 is a schematic diagram of an arterial pressure signal provided in the disclosure.

Exemplarily, referring to FIG. 2, FIG. 2 is a schematic diagram of an arterial pressure signal provided in the disclosure. Arterial pressure signals that vary with respiration are provided in FIG. 2, where each signal wave is an arterial pressure signal. Due to respiratory changes of the subject, the arterial pressure signal is a dynamic signal, and a magnitude of the signal is variable with respiration.

In some embodiments, the breathing signal is used to describe a breathing state of the subject, including but not limited to a respiratory cycle and a respiratory amplitude, where the respiratory cycle is a period for the subject to complete one expiration and one inspiration during breathing, and the respiratory amplitude is used to characterize a respiratory intensity of the subject. Exemplarily, a greater respiratory intensity, i.e., more air inhaled or exhaled, indicates a greater respiratory amplitude. In this embodiment, the breathing signal may also be other signals that can describe the breathing state of the subject, for example, but not limited to an airway pressure, an airway flow, a carbon dioxide flow, a tidal volume, a thoracic impedance signal, a magnetic signal, and a respiratory acoustic signal.

Figure 3:
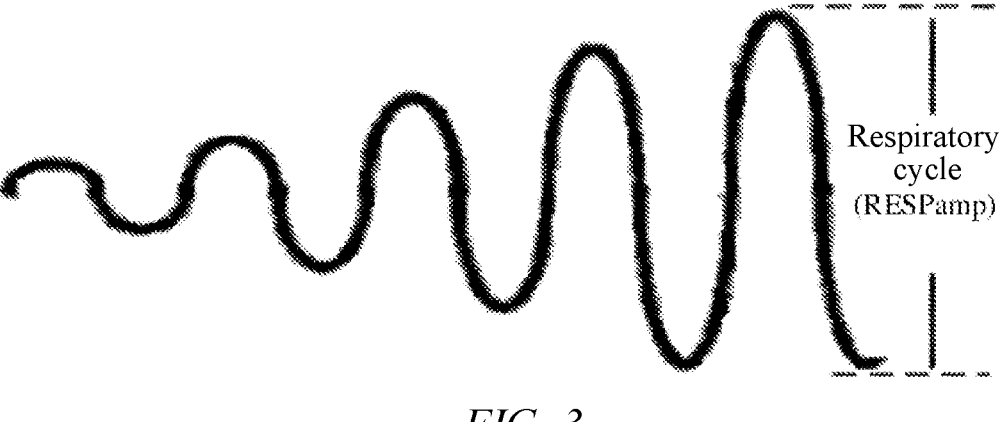
FIG. 3 is a schematic waveform diagram of a breathing signal provided in an embodiment of the disclosure.

The breathing signal acquisition module 110 is configured to obtain the above breathing signals. In some embodiments, breathing signals are extracted from breathing state parameters, i.e., the breathing signal acquisition module 110 is further configured to acquire breathing state parameters of the subject, and extract the breathing signal of the subject based on the acquired breathing state parameters, where the breathing state parameters include at least one of an airway pressure, an airway flow, a carbon dioxide flow, a tidal volume, a thoracic impedance signal, a magnetic signal, and a respiratory acoustic signal. Accordingly, the breathing signal acquisition module 110 may include a device or sensor configured to acquire breathing state parameters and a data processing unit configured to extract breathing signals. The device configured to acquire breathing state parameters may include, for example, but is not limited to, a ventilator, an anesthesia machine, a respiratory impedance tester, a respiratory induction plethysmography system, and a respiratory acoustic detection system. In some embodiments, the breathing signal acquisition module 110 is configured to determine a change rate of breathing state parameters, and determine critical points of exhalations and inhalations based on the change rate, for example, determine nodes where the change rate changes between a negative value and a positive value as critical points of exhalations and inhalations, determine a time cycle of an adjacent inhalation and exhalation as a respiratory cycle, and determine a difference between a maximum value and a minimum value in one respiratory cycle as a respiratory amplitude. Exemplarily, referring to FIG. 3, FIG. 3 is a schematic waveform diagram of a breathing signal provided in an embodiment of the disclosure. In FIG. 3, a crest and a trough are critical points where the change rate changes between a negative value and a positive value. For example, a crest is a critical point at which an inhalation is switched to an exhalation, and a trough is a critical point at which an exhalation is switched to an inhalation. One exhalation and one inhalation form one respiratory cycle (RESPamp), i.e., a time cycle of adjacent crests or adjacent troughs is determined as a respiratory cycle (RESPtime).

In some embodiments, the breathing signal acquisition module 110 is configured to generate respiratory waveforms based on breathing state parameters, determine a respiratory cycle based on a time between two adjacent crests or two adjacent troughs, and determine a respiratory amplitude based on a parameter difference between adjacent crests and troughs. Exemplarily, reference is made to FIG. 3, which will not be repeated herein.

In some embodiments, the breathing signal acquisition module 110 is further configured to extract an envelope of breathing state parameters that change over time, determine a respiratory amplitude based on a parameter difference between crests and troughs of the breathing state parameters in the envelope, and determine a respiratory cycle based on a time difference between two adjacent crests or two adjacent troughs in the envelope.

In some embodiments, breathing signals may be determined based on hemodynamic signals. Accordingly, the breathing signal acquisition module 110 is further configured to determine a breathing envelope of the hemodynamic signal based on the acquired hemodynamic signal, and extract the breathing signal of the subject based on the breathing envelope. In some embodiments, the breathing signal acquisition module 110 receives hemodynamic signals acquired by the hemodynamic signal acquisition module 120, determines a breathing envelope of the hemodynamic signals, determines a respiratory cycle based on a time difference between two adjacent crests or two adjacent troughs in the breathing envelope, and determines a respiratory amplitude based on a parameter difference between crests or troughs, where the respiratory amplitude may be positively correlated with the parameter difference between the crests and the troughs.

The breathing signal acquisition module 110 is connected to the fluid responsiveness detection module 130 and sends obtained breathing signals to the fluid responsiveness detection module 130. The hemodynamic signal acquisition module 120 is connected to the fluid responsiveness detection module 130 and sends acquired hemodynamic signals to the fluid responsiveness detection module 130. It should be noted that the hemodynamic signals and the breathing signals each include a time stamp. The fluid responsiveness detection module 130 aligns the breathing signals with the hemodynamic signals based on the time stamp, compares breathing signals and hemodynamic signals with the same time stamp, or compares breathing signals and hemodynamic signals in the same time stamp range (for example, within the respiratory cycle), and determines a fluid responsiveness based on a corresponding relationship between the breathing signals and the hemodynamic signals.

The fluid responsiveness detection module 130 is further configured to determine a respiratory variation of the subject based on the respiratory cycle, determine a hemodynamic variation of the subject based on the respiratory cycle, and determine the fluid responsiveness of the target subject based on the respiratory variation and the hemodynamic variation.

In some embodiments, the respiratory variation is a change in breathing signals or breathing state parameters in different respiratory cycles. In some embodiments, the respiratory variation includes a respiratory variation trend, a respiratory variation rate, and a respiratory variation value. In some embodiments, respiratory variation values in adjacent cycles (for example, the respiratory variation values may be variation values of a tidal volume or variation values of a carbon dioxide flow) are sequentially determined, the respiratory variation trend may be determined based on whether a respiratory variation value is positive or negative. For example, the respiratory variation trend is to increase when the respiratory variation value is positive, and the respiratory variation trend is to decrease when the respiratory variation value is negative. The respiratory variation rate can be determined based on a ratio of the respiratory variation value to the breathing signal value of the respiratory cycle. Exemplarily, referring to FIG. 3, the respiratory amplitude gradually increases as the respiratory cycle changes in FIG. 3, and it can be determined that in FIG. 3, the respiratory variation trend is to gradually increase. The hemodynamic variation is a change in hemodynamic signals in different respiratory cycles. In some embodiments, the hemodynamic variation includes a hemodynamic variation trend, a hemodynamic variation rate, and a hemodynamic variation value. Since multiple hemodynamic signals may be included in a respiratory cycle, an average or median value of multiple hemodynamic signals in a respiratory cycle may be used to represent a hemodynamic signal value of the respiratory cycle. The hemodynamic variation value is determined based on a hemodynamic signal value of adjacent respiratory cycles, and the respiratory variation trend may be determined based on whether a hemodynamic variation value is positive or negative. For example, the hemodynamic variation trend is to increase when the hemodynamic variation value is positive, and the hemodynamic variation trend is to decrease when the hemodynamic variation value is negative. The hemodynamic variation rate is determined based on a ratio of the hemodynamic variation value to the hemodynamic signal value of the respiratory cycle.

The fluid responsiveness detection module 130 is further configured to perform one of the following operations: determining the fluid responsiveness of the subject based on the respiratory variation trend and the hemodynamic variation trend; determining the fluid responsiveness of the subject based on the respiratory variation rate and the hemodynamic variation rate; and determining the fluid responsiveness of the subject according to the respiratory variation value and the hemodynamic variation value. The subject is determined to exhibit good fluid responsiveness when it is determined that the hemodynamic variation and the respiratory variation meet variation correlation conditions of the hemodynamic signal and the breathing signal; and the subject is determined to exhibit poor fluid responsiveness when it is determined that the hemodynamic variation and the respiratory variation do not meet variation correlation conditions of the hemodynamic signal and the breathing signal. The variation correlation conditions are determined based on the compared hemodynamic signal and the breathing signal, and the variation correlation conditions may be different when the compared hemodynamic signal and the breathing signal are different. Exemplarily, when the hemodynamic signal is an arterial pressure and the breathing signal is a respiratory amplitude, the fluid responsiveness detection module 130 is further configured to determine a respiratory amplitude variation of the subject based on the respiratory cycle, determine an arterial pressure variation of the subject based on the respiratory cycle, and determine the fluid responsiveness of the subject based on the respiratory amplitude variation and the arterial pressure variation. In some embodiments, the fluid responsiveness of the subject is determined based on the respiratory variation trend and the hemodynamic variation trend. When the respiratory amplitude variation trend is the same as the arterial pressure variation trend, it is determined that the subject has good fluid responsiveness; and when the respiratory amplitude variation trend is different from or opposite to the arterial pressure variation trend, it is determined that the subject has poor fluid responsiveness. In some embodiments, determining the fluid responsiveness of the subject based on the respiratory variation rate and the hemodynamic variation rate may be to determine in the same respiratory cycle, whether the hemodynamic variation rate is within the hemodynamic variation rate range corresponding to the respiratory variation rate; if so, it is determined that the subject has good fluid responsiveness, and if not, it is determined that the subject has poor fluid responsiveness. The hemodynamic variation rate range corresponding to respiratory variation rate may be determined based on accuracy of the fluid responsiveness detection, and may be preset.

In some embodiments, the respiratory variation is a change in adjacent breathing signals, the respiratory variation trend of the breathing signals in a preset period is determined based on adjacent breathing signal values, and the respiratory variation rate of breathing signals in the preset period is determined based on variation values of the adjacent breathing signal values. Accordingly, the hemodynamic variation is a change in adjacent hemodynamic signals. The hemodynamic variation trend of hemodynamic signals in adjacent preset periods is determined based on adjacent hemodynamic signal values, and the hemodynamic variation rate of hemodynamic signals in a preset period is determined based on variation values of the adjacent hemodynamic signal values. Exemplarily, in FIG. 3, the respiratory variation trend in each respiratory cycle is to increase first and then decrease; and in FIG. 2, the hemodynamic variation trend (PPV1, PPV2, PPV3 and PPV4) of adjacent hemodynamic signals is determined in each respiratory cycle. It can be seen that the hemodynamic variation trend of each respiratory cycle is to increase first and then decrease. The fluid responsiveness detection module 130 may determine the fluid responsiveness based on a respiratory variation and hemodynamic variation of a corresponding respiratory cycle. In some embodiments, it is possible to determine the fluid responsiveness of the subject based on the respiratory variation trend and hemodynamic variation trend of a corresponding respiratory cycle, or determine the fluid responsiveness of the subject based on the respiratory variation rate and hemodynamic variation rate of a corresponding respiratory cycle, or determine the fluid responsiveness of the subject based on the respiratory variation value and the hemodynamic variation value of a corresponding respiratory cycle. Exemplarily, it is possible to determine the respiratory variation (such as a respiratory variation trend, a respiratory variation rate or a respiratory variation value) in a process of switching a machine-controlled breathing airway flow from a normal mode to a mode with a breathing airway flow of 0 and then to the normal mode, or determine the respiratory variation and the corresponding hemodynamic variation value (PPVn-PPVm) in a process of switching a machine-controlled breathing tidal volume from a normal mode to a mode with the breathing tidal volume being 8 ml/kg and then to the normal mode, where PPVn and PPVm respectively correspond to hemodynamic variations and respiratory variations in different breathing states. It is determined that the subject has good fluid responsiveness when both a respiratory variation and a hemodynamic variation in a preset period meet variation correlation conditions of hemodynamic signals and breathing signals, and it is determined that the subject has poor fluid responsiveness when respiratory variations and hemodynamic variations in one respiratory cycle or a preset number of respiratory cycles do not meet variation correlation conditions of hemodynamic signals and breathing signals.

In some embodiments, it is possible to determine the fluid responsiveness based on any breathing signal (a respiratory amplitude, an airway pressure, an airway flow, a carbon dioxide flow, a tidal volume, a thoracic impedance signal, a magnetic signal, and a respiratory acoustic signal) and any hemodynamic signal (a CVP, an SV, a POP, a PI, an SAP, a PP, a PEP, an inferior or superior vena cava diameter, and an aortic blood flow rate). In this embodiment, after the fluid responsiveness of the subject is determined based on any one of the breathing signals and any one of the hemodynamic signals, the determined fluid responsiveness can be verified based on other combinations of the breathing signals and hemodynamic signals. Exemplarily, when it is determined that the subject has poor fluid responsiveness based on a respiratory amplitude and an arterial pressure, multiple combinations of breathing signals and hemodynamic signals can be selected to re-determine the fluid responsiveness of the subject to prevent inspection errors caused by accidental events.

According to the technical solution provided in this embodiment, dynamic hemodynamic signals and dynamic breathing signals of the subject are acquired in a spontaneous breathing mode, a spontaneous breathing and machine-controlled breathing mode or a machine-controlled breathing mode. The fluid responsiveness of the subject is determined based on a combination of the hemodynamic signals and the breathing signals, so that limitations on breathing in the conventional test are overcome, the fluid responsiveness of the subject in a real breathing state is determined, application ranges of the measured fluid responsiveness is expanded, and accuracy thereof is improved.

Figure 4:
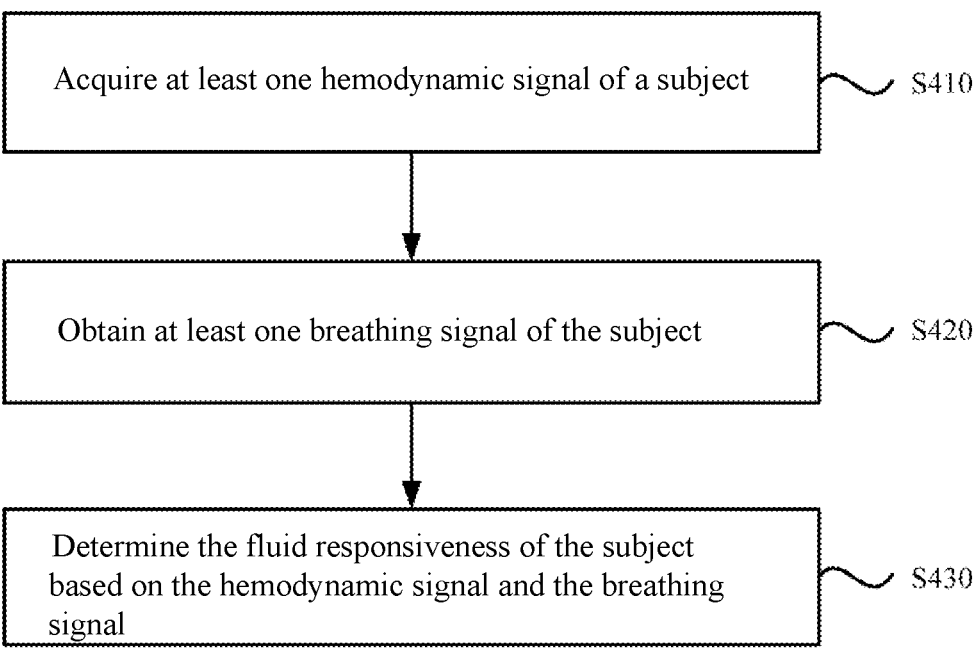
FIG. 4 is a schematic flow diagram of a fluid responsiveness detection method provided in an embodiment of the disclosure.

FIG. 4 is a fluid responsiveness detection method provided in an embodiment of the disclosure. The method is suitable for detecting a fluid responsiveness in a breathing model in a spontaneous breathing mode, a spontaneous breathing and machine-controlled breathing mode, or a machine-controlled breathing mode. In any one of the spontaneous breathing mode, the spontaneous breathing and machine-controlled breathing mode, and the machine-controlled breathing mode, the method includes step S410 to step S430.

In step S410, at least one hemodynamic signal of a subject is acquired.

In step S420, at least one breathing signal of the subject is obtained.

In step S430, the fluid responsiveness of the subject is determined based on the hemodynamic signal and the breathing signal.

In this embodiment, when the breathing of the subject is variable, dynamic breathing signals and dynamic hemodynamic signals changing with the breathing signals are acquired, where the hemodynamic signals and the breathing signals each carry a time stamp, the hemodynamic signals and the breathing signals with the same time stamp or in the same time stamp range are compared based on the time stamp, and the fluid responsiveness of the subject is determined based on the comparison.

The hemodynamic signals may be acquired by a hemodynamic signal acquisition device, and the breathing signals may be obtained by acquiring breathing state parameters of the subject and extraction based on the acquired breathing state parameters, where the breathing state parameters include at least one of an airway pressure, an airway flow, a carbon dioxide flow, a tidal volume, a thoracic impedance signal, a magnetic signal, and a respiratory acoustic signal. The breathing signals may further be obtained by determining a breathing envelope of the hemodynamic signals based on the acquired hemodynamic signals, and performing extraction based on the breathing envelope.

In some embodiments, the breathing signal includes a respiratory cycle, and accordingly, determining the fluid responsiveness of the subject based on the hemodynamic signal and the breathing signal includes: determining a respiratory variation of the subject based on the respiratory cycle; determining a hemodynamic variation of the subject based on the respiratory cycle; and determining the fluid responsiveness of the subject based on the respiratory variation and the hemodynamic variation. Exemplarily, the respiratory variation may be a tidal volume variation, a carbon dioxide flow variation, an airway pressure variation, an airway flow variation, a thoracic impedance signal variation, a magnetic signal variation or a respiratory acoustic signal variation or the like in adjacent respiratory cycles of the subject. Accordingly, the hemodynamic variation may be a variation in dynamic parameters such as a central venous pressure variation ($\Delta$CVP), a stroke volume variation (SVV), a pulse oximetry plethysmograph variation (POPV), a perfusion index variation (Ply), a systolic arterial pressure variation (SAPV), a pulse pressure variation (PPV), a pre-ejection period variation (PEPV), an inferior or superior vena cava diameter variation dIVC/dSVC, an aortic blood flow rate variation $\Delta$Vpeak, etc. The fluid responsiveness of the subject is determined based on any of the above-mentioned respiratory variations and any of the above-mentioned hemodynamic variations described above. In some embodiments, the respiratory variation includes a respiratory variation trend, a respiratory variation rate, and a respiratory variation value, and the hemodynamic variation includes a hemodynamic variation trend, a hemodynamic variation rate, and a hemodynamic variation value. Accordingly, it is possible to determine the fluid responsiveness of the subject based on any of the above-mentioned respiratory variation trends and any of the above-mentioned hemodynamic variation trends, or determine the fluid responsiveness of the subject based on any of the above-mentioned respiratory variation rates and any of the above-mentioned hemodynamic variation rates, or determine the fluid responsiveness of the subject based on any of the above-mentioned respiratory variation values and any of the above-mentioned hemodynamic variation values.

In some embodiments, determining the fluid responsiveness of the subject based on a respiratory variation of the hemodynamic signal includes: determining that the subject has good fluid responsiveness when it is determined that the hemodynamic variation and the respiratory variation meet variation correlation conditions of the hemodynamic signal and the breathing signal; and determining that the subject has poor fluid responsiveness when it is determined that the hemodynamic variation and the respiratory variation do not meet variation correlation conditions of the hemodynamic signal and the breathing signal. The variation correlation conditions are related to hemodynamic signals and breathing signals used to determine the fluid responsiveness, and the variation correlation conditions may be different with different combinations of the hemodynamic signals and the breathing signals.

In some embodiments, the breathing signal further includes a respiratory amplitude, and accordingly, determining the fluid responsiveness of the subject based on the hemodynamic signal and the breathing signal includes: determining a respiratory amplitude variation of the subject based on the respiratory cycle; determining a hemodynamic variation of the subject based on the respiratory cycle; and determining the fluid responsiveness of the subject based on the respiratory amplitude variation and the hemodynamic variation. Accordingly, it is determined that the subject has good fluid responsiveness under at least one of the following conditions: it is determined that a hemodynamic variation trend and a respiratory amplitude variation trend meet variation correlation conditions of the hemodynamic signals and the breathing signals; a hemodynamic variation rate and a respiratory amplitude variation rate meet the variation correlation conditions of the hemodynamic signals and the breathing signals; and a hemodynamic variation value and a respiratory amplitude variation value meet variation correlation conditions of the hemodynamic signals and the breathing signals.

According to the technical solution provided in this embodiment, dynamic breathing signals and dynamic hemodynamic signals changing with the breathing signals of the subject are acquired in a spontaneous breathing mode, a spontaneous breathing and machine-controlled breathing mode or a machine-controlled breathing mode, and the fluid responsiveness of the subject in the above-mentioned breathing mode is determined based on a combination of the hemodynamic signals and the breathing signals. The fluid responsiveness obtained by monitoring a real breathing state of the subject expands application ranges and accuracy of the measured fluid responsiveness, where fluid responsiveness detection accuracy is improved, and limitations of a conventionally measured fluid responsiveness is overcome.

What is claimed is:

1. A fluid responsiveness detection device, comprising: a breathing signal acquisition module, a hemodynamic signal acquisition module and a fluid responsiveness detection module, wherein the breathing signal acquisition module and the hemodynamic signal acquisition module operate under a plurality of breathing modes of a subject, wherein the plurality of the breathing modes comprise: a spontaneous breathing mode, a spontaneous breathing and machine-controlled breathing mode, or a machine-controlled breathing mode;

the hemodynamic signal acquisition module is configured to acquire at least one hemodynamic signal of the subject;

the breathing signal acquisition module is configured to: obtain at least one breathing signal of the subject, the breathing signal corresponds to a respiratory cycle comprising one expiration and one inspiration of the subject; and the fluid responsiveness detection module is configured to determine a fluid responsiveness of the subject based on the breathing signal and the hemodynamic signal, wherein the fluid responsiveness detection module is further configured to:

calculate respiratory variations and hemodynamic variations of the subject based on the breathing signals and the hemodynamic signals respectively obtained in N respiratory cycles, wherein N is a positive integer that is at least two and the respiratory variations and the hemodynamic variations represent changes in the breathing signals and the hemodynamic signals between the N respiratory cycles, and determine the fluid responsiveness of the subject based on the respiratory variations and the hemodynamic variations, including:

when the respiratory variations and the hemodynamic variations in the N respiratory cycles meet variation correlation conditions of hemodynamic signals and breathing signals, determine that the subject exhibits good fluid responsiveness; and when the respiratory variations and the hemodynamic variations in the N respiratory cycles do not meet the variation correlation conditions of hemodynamic signals and breathing signals, determine that the subject exhibits poor fluid responsiveness, wherein the fluid responsiveness is configured to determine an applicability of a volume expansion therapy.

2. The fluid responsiveness detection device of claim 1, wherein the breathing signal further comprises a respiratory amplitude.

3. The fluid responsiveness detection device of claim 1, wherein the breathing signal acquisition module is further configured to acquire a breathing state parameter of the subject, and extract the breathing signal of the subject based on the acquired breathing state parameter, wherein the breathing state parameter comprises at least one of an airway pressure, an airway flow, a carbon dioxide flow, a tidal volume, a thoracic impedance signal, a magnetic signal, and a respiratory acoustic signal.

4. The fluid responsiveness detection device of claim 1, wherein:

the breathing signal acquisition module is further configured to determine a breathing envelope of the hemodynamic signal based on the acquired hemodynamic signal, extract the breathing signal of the subject based on the breathing envelope, and determine a respiratory cycle based on a time difference between two adjacent crests or two adjacent troughs in the breathing envelope.

5. The fluid responsiveness detection device of claim 1, wherein the hemodynamic signal comprises at least one of a central venous pressure (CVP), a stroke volume (SV), a pulse oximetry plethysmograph (POP), a perfusion index (PI), a systolic arterial pressure (SAP), a pulse pressure (PP), a pre-ejection period (PEP), an inferior or superior versa cava diameter, and an aortic blood flow rate.

6. The fluid responsiveness detection device of claim 1, wherein the respiratory variation comprises a respiratory variation trend, a respiratory variation rate, and a respiratory variation value, and the hemodynamic variation comprises a hemodynamic variation trend, a hemodynamic variation rate, and a hemodynamic variation value;

the fluid responsiveness detection module is further configured to perform one of the following operations:

determining the fluid responsiveness of the subject based on the respiratory variation trend and the hemodynamic variation trend;

determining the fluid responsiveness of the subject based on the respiratory variation rate and the hemodynamic variation rate; and determining the fluid responsiveness of the subject according to the respiratory variation value and the hemodynamic variation value.

7. The fluid responsiveness detection device of claim 1, wherein the fluid responsiveness detection module is further configured to determine whether the subject has good fluid responsiveness based on whether the hemodynamic variation and the respiratory variation meet variation correlation conditions of the hemodynamic signal and the breathing signal.

8. The fluid responsiveness detection device of claim 2, wherein the fluid responsiveness detection module is further configured to calculate a variation of the respiratory amplitude of the subject based on the respiratory amplitudes respectively obtained in the different respiratory cycles, and determine the fluid responsiveness of the subject based on the variation of the respiratory amplitude and the hemodynamic variation.

9. The fluid responsiveness detection device of claim 1, wherein the N respiratory cycles comprise adjacent respiratory cycles.

10. A fluid responsiveness detection method, comprising:

in switching among a plurality of breathing modes of a spontaneous breathing mode, a spontaneous breathing and machine-controlled breathing mode, or a machine-controlled breathing mode, acquiring at least one hemodynamic signal of a subject in different respiratory cycles;

obtaining at least one breathing signal of the subject in different respiratory cycles;

calculating respiratory variations and hemodynamic variations of the subject based on the breathing signals and the hemodynamic signals respectively obtained in N respiratory cycles, wherein N is a positive integer that is at least two and the respiratory variations and the hemodynamic variations represent changes in the breathing signals and the hemodynamic signals between the N respiratory cycles;

determining the fluid responsiveness of the subject based on the hemodynamic variations and the respiratory variations, including:

when the respiratory variations and the hemodynamic variations in the N respiratory cycles meet variation correlation conditions of hemodynamic signals and breathing signals, determine that the subject exhibits good fluid responsiveness; and when the respiratory variations and the hemodynamic variations in the N respiratory cycles do not meet the variation correlation conditions of hemodynamic signals and breathing signals, determine that the subject exhibits poor fluid responsiveness, wherein the fluid responsiveness is configured to determine an applicability of a volume expansion therapy.

11. The fluid responsiveness detection method of claim 10, wherein:

when the breathing signal further comprises a respiratory amplitude, the respiratory variation comprises a variation of the respiratory amplitude; and calculating a variation of the respiratory amplitude of the subject based on the respiratory amplitudes respectively obtained in the different respiratory cycles; and determining the fluid responsiveness of the subject based on the variation of the respiratory amplitude and the hemodynamic variation.

12. The fluid responsiveness detection method of claim 10, wherein determining the fluid responsiveness of the subject based on the hemodynamic variation and the respiratory variation of the subject comprises:

determining whether the subject has good fluid responsiveness based on whether the hemodynamic variation and the respiratory variation meet variation correlation conditions of the hemodynamic signal and the breathing signal.

13. The fluid responsiveness detection method of claim 10, wherein the respiratory variation comprises a respiratory variation trend, a respiratory variation rate, and a respiratory variation value, and the hemodynamic variation comprises a hemodynamic variation trend, a hemodynamic variation rate, and a hemodynamic variation value.

14. The fluid responsiveness detection method of claim 10, wherein the N respiratory cycles comprise adjacent respiratory cycles.

15. The fluid responsiveness detection method of claim 10, further comprising:

determining a breathing envelope of the hemodynamic signal based on the acquired hemodynamic signal;

extracting the breathing signal of the subject based on the breathing envelope; and determining a respiratory cycle based on a time difference between two adjacent crests or two adjacent troughs in the breathing envelope.

* * * * *